(12) United States Patent
Caputo

(10) Patent No.: US 7,892,297 B2
(45) Date of Patent: Feb. 22, 2011

(54) CYANIN-TYPE COMPOUNDS HAVING AN ALKYNYL LINKER ARM

(75) Inventor: Giuseppe Caputo, Turin (IT)

(73) Assignee: Cyanine Technologies S.p.A., Torino TO (IT)

(*) Notice: Subject to any disclaimer, the term of this patent is extended or adjusted under 35 U.S.C. 154(b) by 35 days.

(21) Appl. No.: 10/568,159

(22) PCT Filed: Aug. 11, 2004

(86) PCT No.: PCT/IB2004/051447

§ 371 (c)(1),
(2), (4) Date: Feb. 13, 2006

(87) PCT Pub. No.: WO2005/014723

PCT Pub. Date: Feb. 17, 2005

(65) Prior Publication Data

US 2006/0230554 A1 Oct. 19, 2006

(30) Foreign Application Priority Data

Aug. 12, 2003 (IT) .......................... PZ2003A0002

(51) Int. Cl.
C09B 7/00 (2006.01)
C07D 209/30 (2006.01)
(52) U.S. Cl. .................... 8/653; 430/138; 548/455; 548/469
(58) Field of Classification Search ............ 548/455, 548/469, 427; 530/350; 430/138
See application file for complete search history.

(56) References Cited

U.S. PATENT DOCUMENTS 3,925,416 A    12/1975   Akamatsu et al.
6,136,612 A *  10/2000   Della Ciana et al. ........ 436/546
6,716,994 B1    4/2004   Menchen et al.
2002/0051926 A1* 5/2002  Takashima et al. .......... 430/138
2002/0065421 A1* 5/2002  Caputo et al. .............. 548/427
2003/0225247 A1* 12/2003 Stavrianopoulos et al. .. 530/350

FOREIGN PATENT DOCUMENTS

GB    2341 189 A       3/2000
WO    WO 00/75237 A2   12/2000

OTHER PUBLICATIONS

Hermanson, Bioconjugate Techniques, (1996), p. 228-229, and 287.*

* cited by examiner

Primary Examiner—Yong Chu
(74) Attorney, Agent, or Firm—Hasse & Nesbitt LLC; Daniel F. Nesbitt

(57) ABSTRACT

Cyanine-type fluorescent dyes modified with an alkynyl linker arm of formula (I), suitable for the conjugation of biomolecules, such as for example nucleosides, nucleotides, oligonucleotides, nucleic acids, proteins, peptides, vitamins and hormones. A method and intermediates for the synthesis of the alkynyl cyanines of the invention are also described, as well as alkynyl cyanine-biomolecule conjugates and methods for preparing thereof. The alkynyl cyanines can be advantageously used as markers for biomolecules or as quenchers.

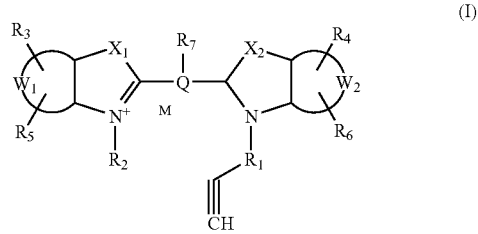

4 Claims, No Drawings

CYANIN-TYPE COMPOUNDS HAVING AN ALKYNYL LINKER ARM

CROSS REFERENCE TO RELATED APPLICATIONS

This is the National Stage of International Application PCT/IB2004/051447, with an international filing date of Aug. 11, 2004, and which claims the benefit of Italian Patent Application No. PZ2003A000002, filed Aug. 12, 2003.

The present invention concerns cyanine type fluorescent dyes having an alkynyl linker arm, their synthesis and their use in bioconjugation and fluorescent labelling of biomolecules such as, e.g., nucleosides, nucleotides, nucleic acids (DNA, RNA or PNA) and proteins, as well as their use in the synthesis of large "Stokes shift" fluorescent dyes.

Furthermore in some embodiments the cyanines of the invention are suitable for use in the double labelling of both nucleic acids and proteins or other biomolecules. In other embodiments the cyanines of the invention are suitable for use as quenchers, i.e., molecules capable of quenching the fluorescence emitted by fluorophores, to be used in structures of the type "molecular beacons".

The use of fluorescence technology has become widespread in the areas of molecular biology, genomics, proteomics and analytical chemistry, since it enables very sensitive and specific test to be carried out, competing effectively with radiolabelling and enzymatic labelling techniques.

DNA probes labelled with fluorescent dyes are valuable reagents for the analysis and separation of molecules. Specific applications of such fluorescent probes include:
1. automated DNA sequencing and mapping;
2. determination of the concentration of a substance that binds to a second species, e.g. DNA hybridisation reactions, in techniques like real time PCR and molecular recognition via molecular beacons;
3. localization of biomolecules in cells, tissues or insoluble supports by techniques such as fluorescence staining.

Also protein labelled with fluorescent substances are very powerful analytical tools used in techniques such as fluorescence microscopy, fluorescence immunoassays, protein chips, laser induced fluorescence capillary electrophoresis.

Recently, techniques making use of probes containing marker pairs, one of which is a fluorescence emitter and the other is a quencher, established themselves for the detection of nucleic acids. The two molecules are, e.g., conjugated to the ends of an oligonucleotidic probe having a central target nucleic acid binding sequence. The oligonucleotide probe takes on a closed loop conformation by virtue of the presence of two short complementary base sequences (generally 5 to 10 bases each) flanking the central target binding sequence. In the absence of the target the two flanking sequences are capable of originating an intramolecular base pairing hybridized structure, in which the quencher is proxymal to the fluorophore, thereby quenching its fluorescence. When the oligonucleotide probe finds a target sequence complementary to its own central binding sequence, it unfolds to hybridize with it, and the fluorophore and the quencher space out so that the quencher is no longer able to quench the fluorescence emitted by the fluorophore, thus allowing the detection of the emitted fluorescence in the presence of the target.

Among fluorescent dyes, cyanines have wide application as biomolecule labels in several bioanalytical techniques thanks to their chemical-physical properties such as the high extinction coefficient, high quantum yield, independence of pH, low molecular weight and the possibility to perform multiple assays simultaneously using multiple fluorophores emitting at different wavelengths. The cyanines can be also used as quenchers if their structure contains, for instance, nitro groups.

To be useful as a fluorescent label or as a quencher for bioconjugations, a dye has to be provided with a suitable linker arm containing a functional group to give rise to a covalent link with the biomolecule which is to be labelled. While the chromogenic part of the dye structure is generally known, the introduction of a functionalized linker arm for the purpose of conjugation with another molecule, represents the innovative step in a number of inventions concerning the use of fluorescent dyes as labelling reagents. The research in this field is therefore focused on innovative functionalized arms, since the chemistry and the behaviour of such functionalized arms can remarkably affect the fluorescence of the whole molecule as well as several physical and chemical characteristics such as hydrophobicity/hydrophilicity, stacking and intramolecular quenching.

In general, the presence of only one functionalized linker arm is preferable, in order to avoid cross-linking between multiple similar molecules, undesired multiple reactions or purification problems.

The synthesis of biomolecules labelled with fluorescent compounds, e.g. nucleotides, requires several steps among which the separate synthesis of a functionalized nucleotide and of a functionalized fluorescent molecule and their subsequent conjugation.

Several kinds of functionalized linker arms suitable for the conjugation of biomolecules with fluorescent compounds are described in the prior art.

For instance U.S. Pat. No. 5,486,616 describes a method for labelling biomolecules with water soluble cyanines containing a functionalized linker arm consisting of an alkyl chain terminating with a functional group selected e.g. among isothiocyanate, isocyanate, monochlorotriazine, dichlorotriazine, mono- or di-halogen substituted pyridine, mono- or di-halogen substituted diazine, maleimide, aziridine, sulphonyl chloride, acyl chloride, hydroxysuccinimidyl ester, hydroxysulfosuccinimidyl ester, imidic ester, hydrazine, azidonitrophenyl, azide, 3-(2-pyridyldithio)-propionamide, glyoxal, aldehyde.

Furthermore, U.S. Pat. No. 5,047,519 discloses a method for preparing fluorescently labelled nucleotides comprising the steps of:
activating the nucleotide towards aromatic nucleophilic substitution by means of the introduction of a iodine atom at the 5 position of a pyrimidine, at the 8 position of a purine or at the 7 position of a 7-deazapurine;
phosphorilation of the iodonucleotide in order to obtain the corresponding triphosphate;
introducing a propargylamino functional group at the activated position by means of a nucleophilic attack following the Heck Pd(0) catalyzed reaction;
synthesizing a fluorescent dye containing a carboxylic acid;
preparing the fluorescent dye active ester in order to activate it towards the acyl nucleophilic substitution reaction;
reacting the propargylamino modified nucleotide with the fluorescent dye active ester.

Alternatively, the functionalized linker arm may contain an acid group, which must be then activated to react with an amine group of the dye molecule to give an amide bond.

Anyway in both cases the activation of the carboxylic acid group, e.g. as active ester, is necessary.

Nevertheless, the use of active esters, and in general of active carboxylic groups, shows considerable disadvantages such as poor stability over time and difficult synthesis. Active esters are, in fact, not much stable molecules if not in perfectly anhydrous conditions and therefore suffer from substantial storage troubles. They tend to degrade over time by hydrolysis and the percentage of active product in a package decreases over time. Furthermore, due to the poor stability, it is virtually impossible to store the unused product still further immediately after opening of the packaging. Moreover, the need to work in perfectly anhydrous conditions makes the synthesis of such compounds difficult and expensive, since the purifications are to be carried out with anhydrous solvents.

An object of the present invention is to provide a fluorescent dye molecule of the type cyanine provided with a linker arm suitable for the conjugation with a biomolecule, such as for example nucleosides, nucleotides, nucleic acids and proteins, which however does not require the formation on an active acid group during the conjugation reaction.

Such object is achieved by a cyanine modified with an alkynyl-linker arm, having the following general formula (I), including the valence tautomers thereof:

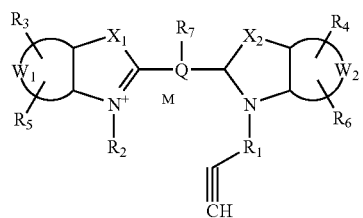

(I)

wherein $R_1$ is a linear, saturated or unsaturated alkyl chain, having from 1 to 30 carbon atoms, wherein one or more carbon atoms are each optionally replaced with a component independently selected from an oxygen or a sulfur atoms, a —NH— or a —CONH— group, or a cyclic, aromatic or not aromatic, 4-, 5- or 6-membered grouping of carbon atoms wherein one or more carbon atoms are each optionally replaced with a heteroatom independently selected from oxygen, sulfur, nitrogen and selenium; $W_1$ and $W_2$ are independently selected from a benzene ring and a naphthalene ring wherein one or more carbon atoms are optionally replaced with one or more heteroatoms selected from oxygen, sulfur, selenium and nitrogen, or one of $W_1$ and $W_2$ is absent, or both of them are absent; $X_1$ and $X_2$ are independently selected from the group consisting of —O—, —S—, —Se—, —N—, —C(CH$_3$)$_2$, —CH=CH—, —NH—, or

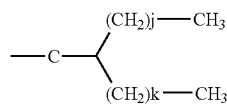

with j=1-20 and k=1-20;

$R_2$, $R_3$, $R_4$, $R_5$ and $R_6$ are independently selected from hydrogen, —COOH, —OH, —NO$_2$, —OCH$_3$, —O$_3$H, —O$_3$, and —R$_8$—Y wherein $R_8$ is a linear, saturated or unsaturated alkyl chain, having from 1 to 30 carbon atoms, wherein one or more carbon atoms are each optionally replaced with a component independently selected from an oxygen or a sulfur atom, a —NH— or a —CONH— group, or a cyclic, aromatic or not aromatic, 4-, 5- or 6-membered grouping of carbon atoms wherein one or more carbon atoms are each optionally substituted by a heteroatom independently selected from oxygen, sulfur, nitrogen or selenium, and wherein Y is selected from the group consisting of hydrogen, carboxyl, carbonyl, amino, sulphydryl, thiocyanate, isotyocianate, isocyanate, maleimide, hydroxyl, phosphoramidite, glycidyl, imidazolyl, carbamoyl, anhydride, bromoacetamido, chloroacetamido, iodoacetamido, sulfonyl halide, acyl halide, aryl halide, hydrazide, succinimidyl ester, hydroxysulfosuccinimidyl ester, phthalimidyl ester, naphthalimidyl ester, monochlorotriazine, dichlorotriazine, mono- or di-halide substituted pyridine, mono- or di-halide substituted diazine, aziridine, imidic ester, hydrazine, azidonitrophenyl, azide, 3-(2-pyridyldithio)-propionamide, glyoxal, aldehyde, nitrophenyl, dinitrophenyl, trinitrophenyl and —C≡CH;

M is a counterion; and

Q is a polymethinic chain selected from:

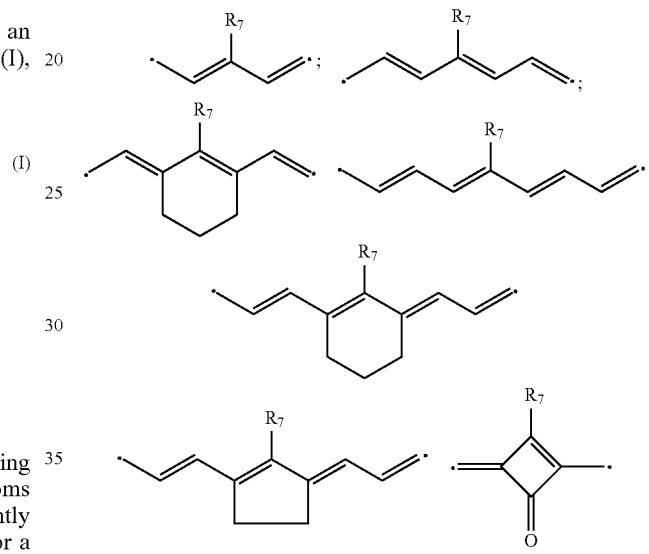

wherein $R_7$ is selected from the group consisting of hydrogen, fluorine, chlorine, bromine, iodine, phenoxy, thiophenoxy, anilino, cyclohexylamino, pyridine, —R$_8$—Y, —O—R$_8$—Y, —S—R$_8$—Y, —NH—R$_8$—Y, wherein $R_8$ e Y are as defined above, and aryl optionally substituted with one or more substituents independently selected from the group consisting of —SO$_3$H, carboxyl (—COOH), amino (—NH$_2$), carbonyl (—CHO), thiocyanate (—SCN), isothiocyanate (—CNS), epoxy and —COZ wherein Z represents a leaving group.

Suitable leaving groups are for example —Cl, —Br, —I, —OH, —OR$_{11}$, —OCOR$_{11}$, wherein $R_{11}$ is linear or branched lower C$_1$-C$_4$ alkyl (for example methyl, ethyl, t-butyl or isopropyl), —O—CO—Ar, wherein Ar is optionally substituted aryl; —O—CO—Het, wherein Het is selected from succinimide, sulfosuccinimide, phthalimide and naphthalimide, —NR$_{22}$R$_{33}$, wherein $R_{22}$ and $R_{33}$ are each independently linear or branched C$_1$-C$_{10}$ alkyl.

As used above, the expression "carbon atom optionally replaced with" means that such carbon atom in the linear alkyl chain or in the cyclic grouping of atoms can be replaced by one of the components or heteroatoms indicated above.

In the following of the description, the cyanines having an alkynyl linker arm of the present invention illustrated by formula (I) will be referred to as "alkynyl cyanines".

Preferred examples of alkynyl cyanines which fall within the scope of the present invention are:

Formula (Ia)
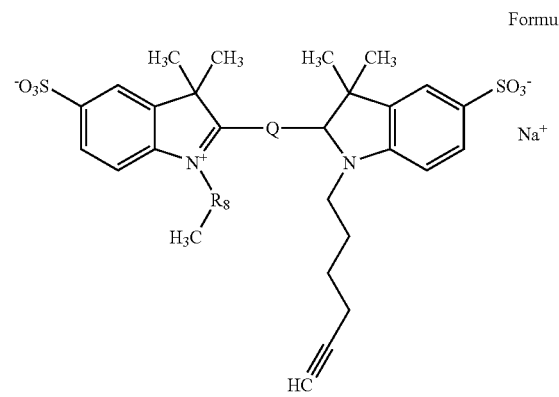
Formula (Ib)
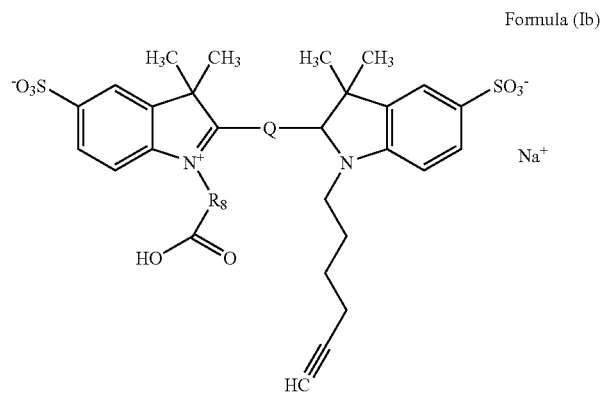
Formula (Ic)
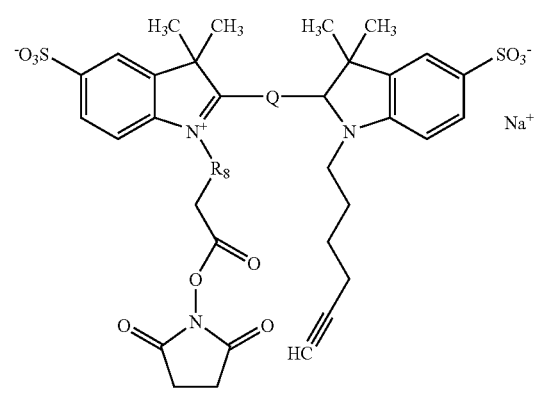
Formula (Id)
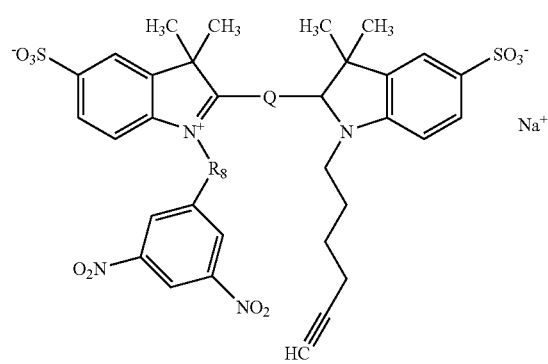
Formula (Ie)
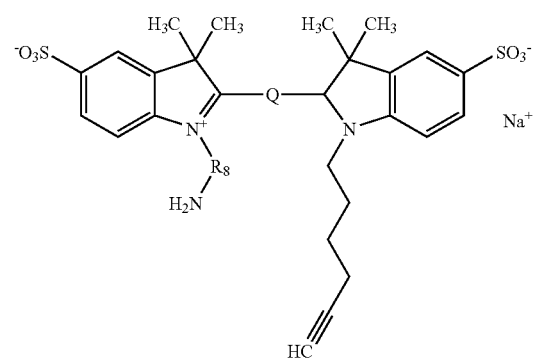
Formula (If)
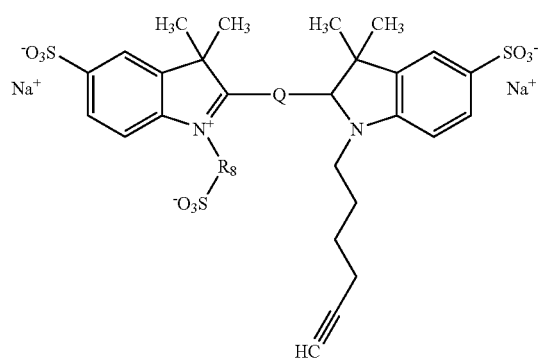
Formula (Ig)
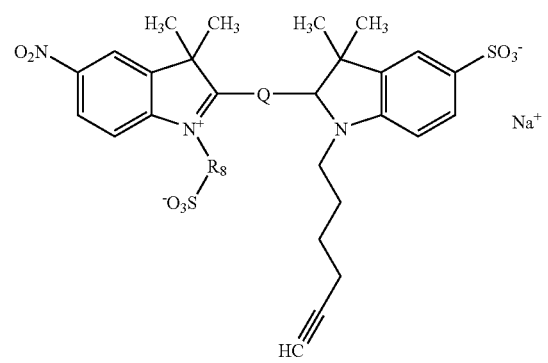
Formula (Ih)
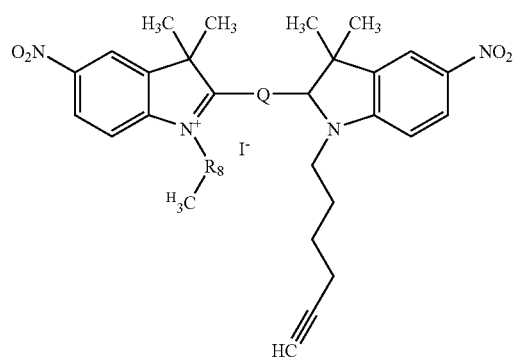

-continued
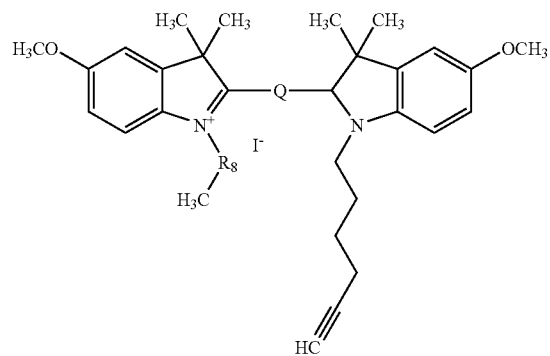
Formula (Ii)
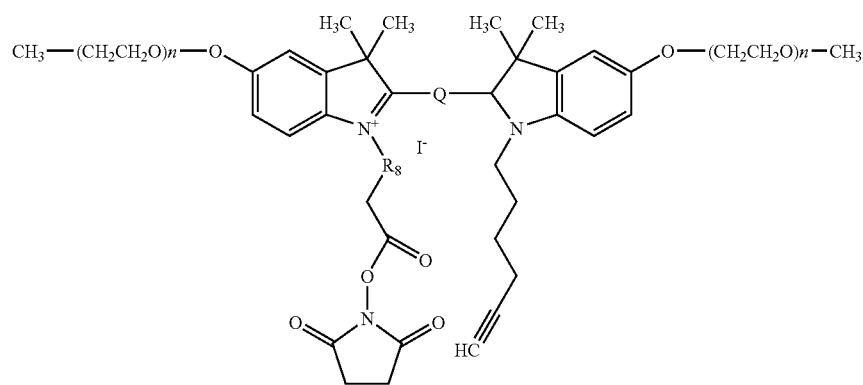
Formula (Il)
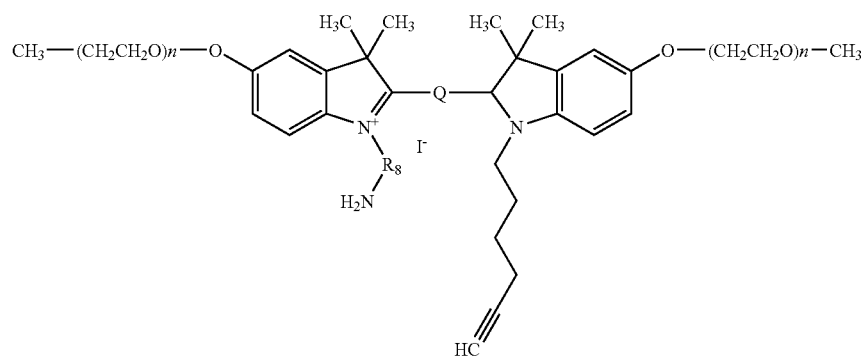
Formula (Im)
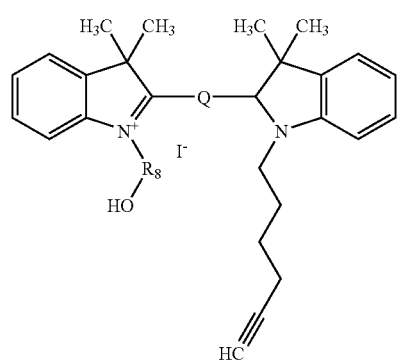
Formula (In)

wherein Q and $R_8$ are as defined above for formula (I) an n is an integer comprised between 1 and 100.

The alkynyl cyanines of the present invention are synthetized according to a reaction scheme which comprises the following steps:
1. synthesis of the quaternary ammonium salt
2. synthesis of a second quaternary ammonium salt
3. synthesis of the hemicyanine
4. synthesis of the cyanine Step 1 is carried out by reacting in a suitable solvent, such as sulfolane, acetonitrile or N,N-dimethylformamide, a nitrogen-containing heterocyclic system with a molecule which contains a terminal triple bond to form the alkynyl quaternary ammonium salt:

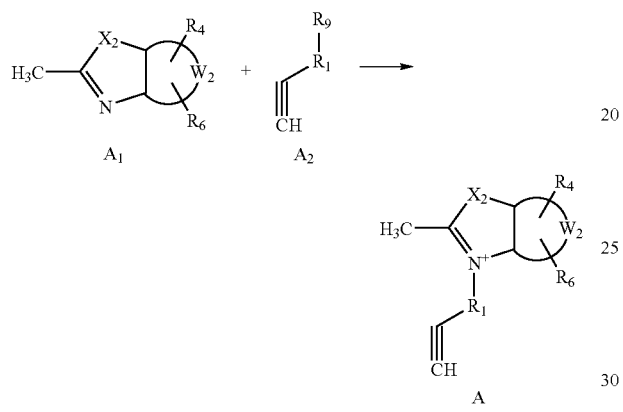

wherein $X_2$, $R_1$, $R_4$, $R_6$ e $W_2$ are as defined above for formula (I), and $R_9$ is selected from the group consisting of iodine, chlorine, bromine, OH, sulphate and tosylate.

Step 2 consists of the synthesis of a second quaternary ammonium salt starting from a second nitrogen-containing heterocyclic system and from an alkylating molecule $R_2$-$R_9$ according to the scheme:

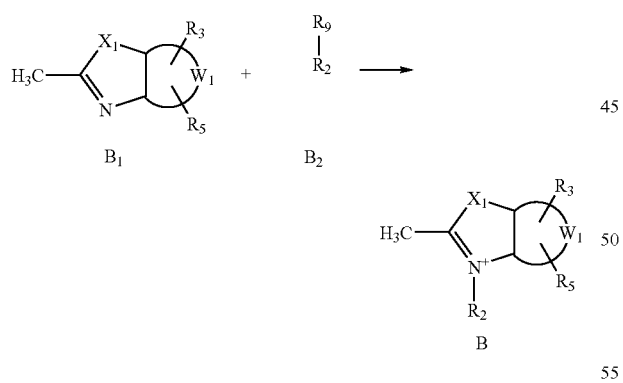

wherein $X_1$, $R_2$, $R_3$, $R_5$ e $W_1$ are as defined above for formula (I), and $R_9$ is selected from the group consisting of iodine, chlorine, bromine, OH, sulphate, tosylate.

Step 3 can be carried out either on the alkynyl-quaternary ammonium salt A of step 1 or on the quaternary ammonium salt B synthetized in step 2. It consists of the reaction of A or B with a compound capable of reacting with the heterocyclic quaternary ammonium salt to form a polymethine chain. Non limiting examples of such compounds are triethylorthoformate, N,N-diphenylformamide, malonaldehyde dianil, pyridyl malonaldehyde, trimethoxypropene, 5-phenylamino-2,2-trimethylene-2,4-pentadienylidene phenylammonium chloride, chloromalonaldehyde dianil and squaric acid. From this step, an intermediate named hemicyanine is obtained.

Step 4 is carried out by reacting the hemicyanine obtained in step 3 with the quaternary ammonium salt A or B not used in the preceding step. The desired alkynyl cyanine product is obtained.

In all of the preceding steps the specific reaction conditions depend on the type of the reagents employed in the different steps and on the desired final product.

The alkynyl cyanines of the present invention are particularly suitable for the conjugation of biomolecules, particularly proteins, nucleosides, nucleotides, oligonucleotides and in general with nucleic acids containing bases modified with an halogen atom (for example iodine, chlorine, bromine) at position 5 of pyrimidines, 8 of purines and 7 of 7-deazapurines.

Thus, the scope of the present invention also encompasses an alkynyl cyanine as previously described conjugated through the $R_1$—C≡CH linker arm with a biomolecule selected from the group consisting of nucleosides, nucleotides, oligonucleotides, nucleic acids, for example DNA, RNA or PNA ("peptide nucleic acids"), peptides and proteins.

Such a cyanine conjugated with a biomolecule can be represented by the following general formula (II):

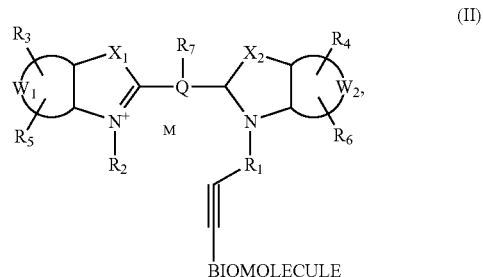

wherein $R_1$, $R_2$, $R_3$, $R_4$, $R_5$, $R_6$, $R_7$, $X_1$, $X_2$, $W_1$, $W_2$, M and Q are as defined for formula (I).

With reference to nucleosides, the general conjugation scheme is as follows:

Scheme 1

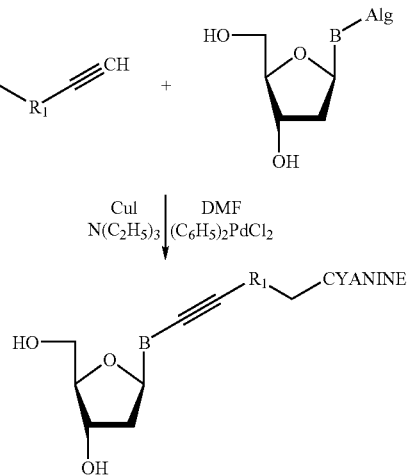

wherein B is a base selected from cytosine, uracil, guanine, adenine, xanthine, hipoxanthine, 7-deazaguanine, 7-deazaadenine, 7-deazaxanthine, 7-deazaipoxanthine, Alg is an halogen selected from iodine, chlorine and bromine, and wherein $R_1$ is as defined in formula (I).

In previous Scheme 1, the alkynyl arm-containing cyanine according to the invention is reacted with the halo-derivative of a nucleoside. Halo-derivatives of nucleotides and nucleosides are commercially available or can be synthetized as described in European patent EP0251786B1.

The reaction is carried out in a suitable anhydrous organic solvent, for example anhydrous N,N-dimethylformamide (DMF), and in the presence of an organic base, such as for example triethylamine ($N(C_2H_5)_3$), and of a Pd(0) compound as the catalyst. Instead of the Pd(0) compound, it is possible to use as the catalyst a Pd(II) compound (for example $(C_6H_5)_2PdCl_2$)) and a co-catalyst capable of forming Pd(0) in situ, such as for example CuI.

The reaction is preferably carried out at room temperature for a period of time of about 8 hours. When the reaction time has passed, a second aliquot of catalyst, organic base and optionally co-catalyst is added to the reaction mixture, then the mixture is left reacting under the same conditions for a further period of time, preferably about 16 hours.

Reaction Scheme 1 also applies to the conjugation of nucleotides, oligonucleotides and nucleic acids (DNA, RNA, PNA).

Alternatively, the cyanine-nucleoside conjugate obtained according to Scheme 1 can be phosphorylated, thereby obtaining a cyanine-nucleotide triphosphate conjugate. Phosphorylation of the cyanine-nucleoside conjugate can be carried out for example using the nucleoside phosphorylation method described in patent EP0251786B1.

The cyanine-nucleotide triphosphate conjugate is a suitable substrate for DNA polymerase and may be used in PCR reactions for the preparation of fluorescent DNA chains.

The scope of the present invention also encompasses an alkynyl cyanine as previously described, conjugated through the $R_1$—C≡CH linker arm with a second fluorescent dye, the second fluorescent dye being capable of emitting fluorescence at a wavelength at which the cyanine is capable of absorbing, or the second fluorescent dye being capable of absorbing at a wavelength at which the alkynyl cyanine is capable of emitting (FRET couples).

Said cyanine conjugated with a second fluorescent dye can be represented by the following general formula (III):

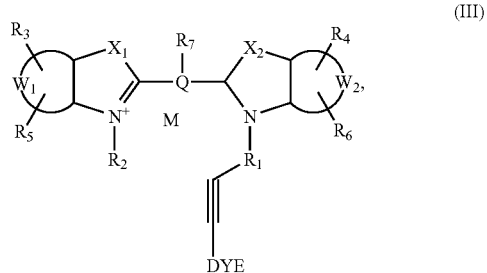

(III)

wherein $R_1$, $R_2$, $R_3$, $R_4$, $R_5$, $R_6$, $R_7$, $X_1$, $X_2$, $W_1$, $W_2$, M and Q are as defined above for formula (I) and DYE is the second dye.

Such conjugates are useful when it is desired to have a fluorescent system with a large Stokes shift in order to have maximum separation between excitation light and emission.

Optical bioanalytical strumentation in fact uses filters in order to optimally separate excitation light from emission, but in the case of fluorophores with a small Stokes shift overlappings may occur which make fluorescence quantification difficult.

One example of a conjugate between a cyanine and a second fluorescent dye forming a large Stokes shift is the compound 1-(4-carboxybutyl)-1'-{6-[N,N'-Difluoroboryl-1,9-dimethyl-5-(4-iodophenyl)-dipyrryl]-es-5-inyl}-3,3,3',3'-tetramethyl-5,5'-disulfo indodicarbocyanine sodium salt of formula:

Formula (IIIa)

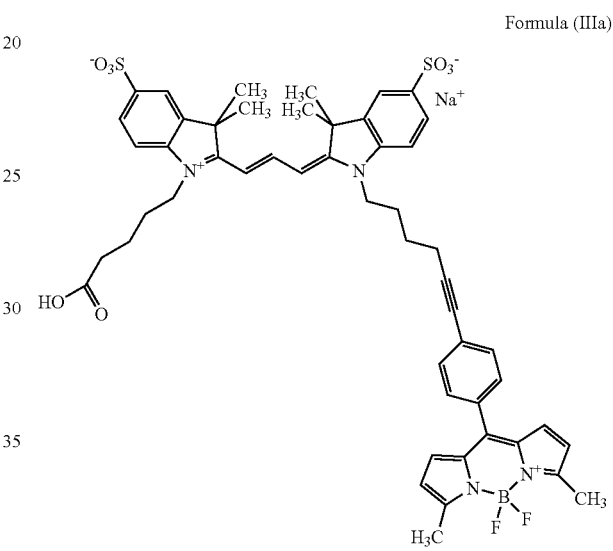

which is obtained by reacting 1-(4-carboxybutyl)-1'-es-5-inyl-3,3,3',3'-tetramethyl-5,5'-disulphonate indodicarbocyanine sodium salt with N,N'-difluoroboryl-1,9-dimethyl-5-(4-iodophenyl)-dipirryne according to a mechanism which is similar to the one described for the conjugation of an alkynyl cyanine with an halo-nucleoside.

Other examples are conjugates obtained by reacting alkynyl cyanines of the general formula (I) with complexes of transition metals (Me) such as ruthenium, osmium, rhenium, iridium, rhodium, platinum, palladium, molibdenum and technetium, having at least a nitrogen-containing heterocyclic linker linked to the cyanine alkynyl linker arm. Nitrogen-containing heterocyclic linkers suitable for this purpose are for example optionally substituted 2,2'-bipiridyne, optionally substituted 1,10-phenantroline, optionally substituted batophenantroline. Suitable substituents for the above mentioned nitrogen-containing heterocyclic linkers are for example iodine, chlorine, bromine, phenyl, trifluoromethyl, or the $R_5$ group defined in formula (I).

A specific non-limiting example of such a conjugate is the compound 1-(4-carboxybutyl)-1'-{6-[(2-2'-bipyridine)$_2$(2-2'bipyridin-4-yl) ruthenium(II)]-es-5-inyl}-3,3,3',3'-tetramethyl-5,5'-disulphonate indodicarbocyanine iodide:

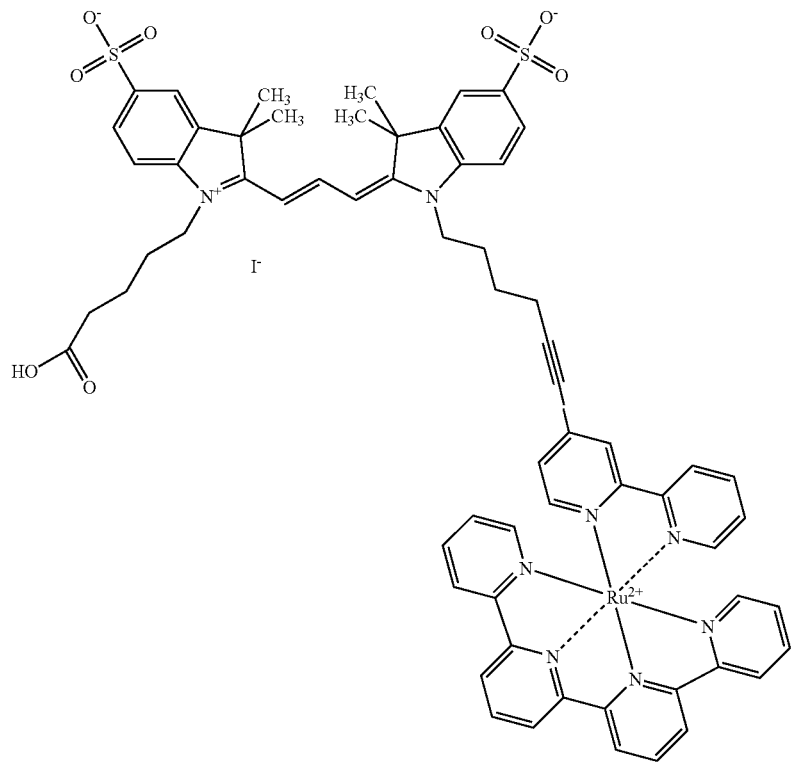

Such a compound is synthetized by reacting the alkynyl cyanine according to the present invention 1-(4-carboxybutyl)-1'es-5-inyl-3,3,3',3'-tetramethyl-5,5'-disulphonate indodicarbocyanine sodium salt with the compound bis(2,2'-bipyridine) (4-iodo-2,2',bipyridine) ruthenium(II) with a procedure similar to the one of Scheme 1 in which the halonucleoside is replaced by the ruthenium complex.

A compound of this type has very interesting optical properties which make it particularly useful as a label in bioanalytical applications.

Further preferred embodiments of the present invention are the alkynyl cyanines illustrated by formula (I) in which one of $R_2$, $R_3$, $R_4$, $R_5$ and $R_6$ is —$R_8$—Y wherein Y is different from H and from —C≡CH. Such cyanines in fact contain a second functional group which is capable of binding to a second biomolecule, for example a protein or a peptide.

Cyanines according to said preferred embodiment are bifunctional molecules, thereby permitting the simultaneous conjugation of two different or similar biomolecules.

Therefore, the scope of the present invention also encompasses a bifunctional alkynyl cyanine conjugated through the —$R_1$—C≡CH linker arm with a first biomolecule selected from the group consisting of nucleotides, nucleosides, nucleic acids, proteins, peptides, vitamins and hormones, and through the —$R_8$—Y linker arm with a second similar or different biomolecule selected from the group consisting of nucleotides, nucleosides, nucleic acids, proteins, peptides, vitamins and hormones.

Such an alkynyl cyanine conjugated with a first and a second biomolecule is represented by the following general formula (IV):

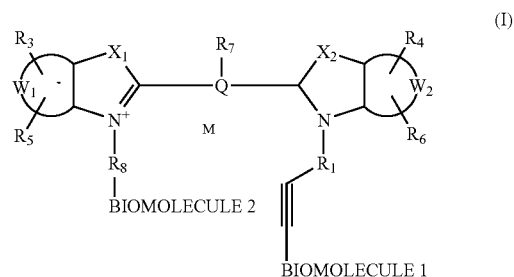

wherein $R_1$, $R_3$, $R_4$, $R_5$, $R_6$, $R_7$, $R_8$, $X_1$, $X_2$, $W_1$, $W_2$, M and Q are as defined for formula (I).

Bifunctional alkynyl cyanines of the invention may be used for example for preparing fluorescent oligonucleotides conjugated with the protein streptavidin, useful for use in molecular recognition assays with signal enhancement. Streptavidin in fact can bind four biotin molecules with high affinity. If every biotin is in turn conjugated with a fluorescent cyanine, the total detectable fluorescent signal will be 5-folds higher, with a remarkable increase in the assay sensitivity. The following scheme shows the structure of the conjugate described above:

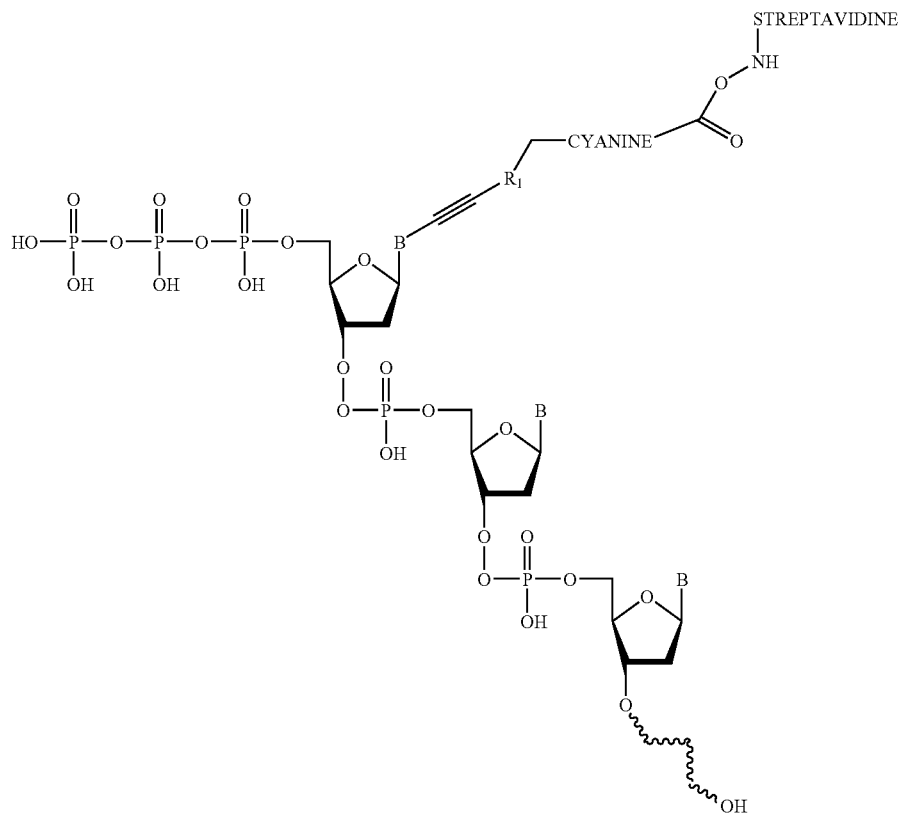

The following examples, which illustrate the synthesis of some embodiments of the present invention, are provided for illustration purposes only and should not be intended to limit the scope of the invention in any way.

EXAMPLE 1

Synthesis of 1-ethyl-1'-(hex-5-ynyl)-3,3,3',3'-tetramethyl-5,5'-disulfo-indomonocarbocyanine potassium salt (Cyanine IRIS 3 sulfo alkynyl) (Compound 1)

a) Synthesis of 6-iodo-hex-1-yne

A mixture of 6-chlorohex-1-yne (10 g, 85.8 mmol) and 71 ml of anhydrous acetone is heated at 70° C. on a water bath for 10 min. in a round-bottom flask fitted with a reflux condenser closed by a calcium chloride trap. Sodium iodide (25.8 g, 172 mmol) is added to the mixture and heating is maintained for 22-24 h. The mixture is then cooled to room temperature and concentrated by distillation. Ether is added and the inorganic salt, which precipitates, is filtered. The residue is poured in a separatory funnel, which is then shaken, successively, with 10% sodium bisulfite sodium bicarbonate solution. It is dried with anhydrous sodium sulfate and the solvent is evaporated under reduced pressure.

b) Synthesis of N-hex-5-ynyl-2,3,3-trimethylindoleninium-5-sulfonate

A mixture of 2,3,3-trimethyl-3H-indolenine-5-sulfonate potassium salt (5.0 g, 18.02 mmol), 6-iodohex-1-yne (22.56 g, 180.2 mmol) and 50 ml of sulfolane is placed in a round-bottom flask fitted with a reflux condenser and refluxed at 120° C. on a water bath for 12 h. The reaction mixture is cooled to room temperature and added dropwise to 800 ml of vigorous stirred diethyl ether. The product is collected on a fritted glass filter, washed with ether and dried in a desiccator under vacuum.

c) Synthesis of 2-{(E)-2-[acetyl(phenyl)amino]vinyl}-1-ethyl-3,3-dimethyl-3H-indolium-5-sulfonate (hemicyanine)

3.00 g of N-ethyl-2,3,3-trimethylindoleniniun-5-sulfonate (8.43 mmol), 3.33 g of N,N-diphenylformamide (16.98 mmol), 6.00 ml of acethylchloride, 60.00 ml of acetic anhydride are placed in a 250 ml round-bottom flask. The mixture is heated at 120° C. for 90 minutes. The orange solution is cooled to room temperature and added dropwise to 300 ml of vigorous stirred diethyl ether. The product is collected on a fritted glass filter, washed with diethyl ether and dried in a desiccator under vacuum. The desired product has an absorbance maximum at 378 nm in methanol. Yield is 97%.

d) Synthesis of cyanine IRIS 3 sulfo alkynyl 5.00 g (12.14 mmol) of the hemicyanine synthesized in the previous step is placed in a 250 ml round-bottom flask together with 3.87 g (12.14 mmol) of N-hex-5-ynyl-2,3,3-trimethylindoleninium-5-sulfonate, 10.80 ml of triethylamine and 109 ml of acetic anhydride and heated at 135° C. for 2 h. The red purple solution is cooled to room temperature and added dropwise to 800 ml of vigorous stirred diethyl ether. The desired product is collected on a fritted glass filter, washed with diethyl ether and dried in a desiccator under vacuum. The product is then purified by flash chromatography using a dichloromethane/methanol mixture gradient from 90/10 to 70/30. Yield is 42%. The product has absorbance maximum in ethanol at 554 nm and emission maximum at 570 nm.

Compound 1

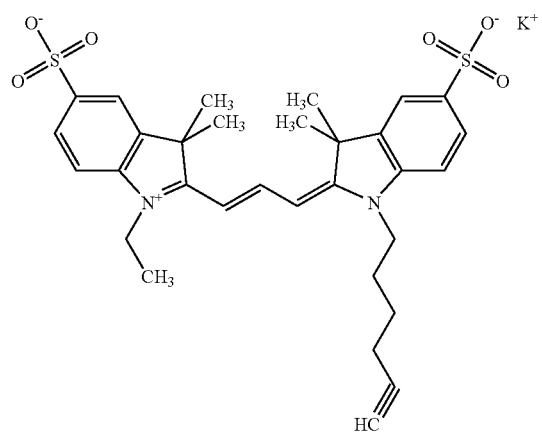

EXAMPLE 2

Synthesis of 5-(cyanine IRIS 3 sulfo alkynyl)-2'-deoxycytidine (Compound 2)

15.6 mg (0.044 mmol) of 5-iodo-2'-deoxy-cytidine and 1.7 mg (0.0088 mmol) of CuI are placed in a vial with magnetic stirrer; 83.2 mg (0.131 mmol) of Compound 1, dissolved in the minimal quantity of anhydrous N,N-dimethylformamide, are added. Argon is refluxed for fifteen minutes. 0.012 mL (0.0088 mmol) of $N(C_2H_5)_3$ and 3.0 mg (0.0044 Mmol) of $(C_6H_5)_2PdCl_2$ are added and argon is refluxed fifteen minutes more. The reaction is conducted for eight hours under stirring at room temperature. When the time has passed, 1.7 mg (0.0088 mmol) of CuI, 0.012 mL of $N(C_2H_5)_3$ and 3.0 mg (0.0044 mmol) of $(C_6H_5)_2PdCl_2$ are added and the reaction is conducted in the same conditions 16 hours more. Purification is carried out on a MPLC column (eluents: $CH_3OH$, $H_2O$).

The product appears as a red coloured powdery solid.

Compound 2

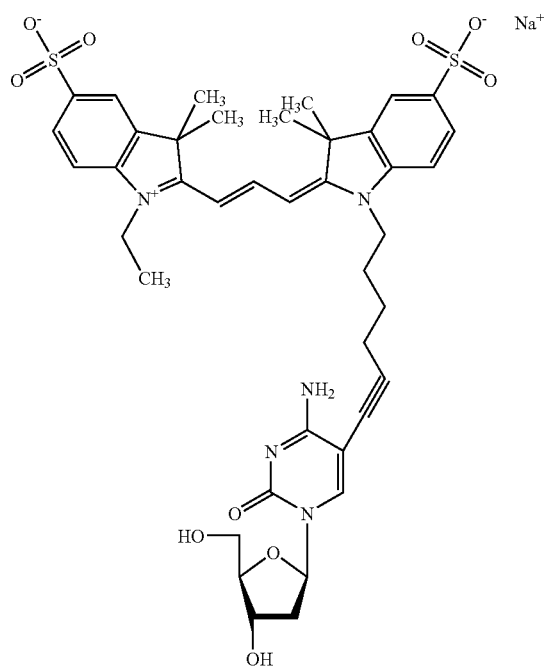

EXAMPLE 3

Synthesis of 5-(cyanine IRIS 3 sulfo alkynyl)-2'-deoxycytidine triphosphate (Compound 3)

59 mg (0.071 mmol) of Compound 2, dissolved in the solvent $(CH_3)_3PO_4$, are placed in the reaction round-bottom flask, and argon is refluxed for the whole length of the reaction. The solution is cooled at $-10°$ C. and 0.007 ml di $POCl_3$ are added. The solution is stirred at $-10°$ C. for thirty minutes, 0.007 ml of $POCl_3$ are then further added and the temperature is slowly raised to room temperature. After 100 minutes from the second $POCl_3$ addition monophosphorilation is complete. The reaction mixture is percolated into a solution of $Na[NH(C_4H_7)_3]P_2O_7$ in N,N-dimethylformamide pre-cooled at $-10°$ C. After 100 minutes the solution is added to $N(C_2H_5)_3$ (0.1 ml) dissolved in water (1.42 ml) pre-cooled at $0°$ C. The solution is stirred on ice for 15 minutes and let to stay at $4°$ C. overnight. Purification is performed on reverse phase MPLC.

Compound 3

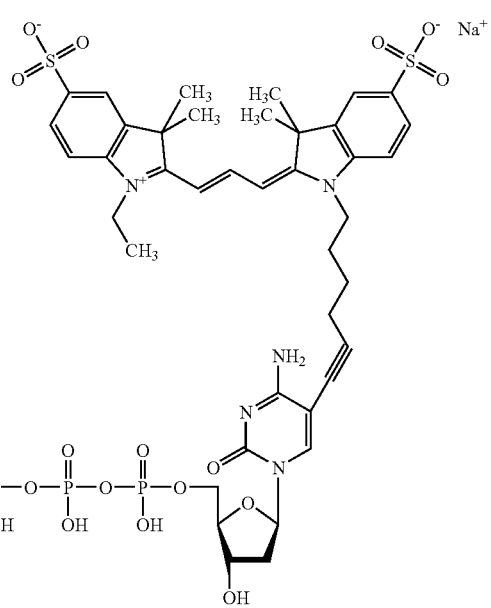

EXAMPLE 4

Synthesis of 1-(4-carboxybutyl)-1'-es-5-ynil-3,3,3', 3'-tetramethyl-5,5'-disulfonated indodicarbocyanine sodium salt (Compound 4)

2.69 g (8.43 mmol) diof N-es-5-ynil-2,3,3-trimethylindoleninium-5-sulfonate, 4.84 g (16.98 mmol) of malonaldehyde dianil (N-[(1Z,2E)-3-anilinoprop-2-enylidene]benzenaminium chloride), 6.0 ml of acetyl chloride and 60.0 mL of acetic anhydride are placed in 250 ml round-bottom flask. The mixture is heated at $120°$ C. for 90 minutes. The orange solution is cooled to room temperature and added dropwise to 300 ml of vigorous stirred diethyl ether. The product (hemicyanine) is collected on a fritted glass filter, washed with diethyl ether and dried in a desiccator under vacuum. The desired product has an absorbance maximum at 378 nm in methanol. Yield is 97%.

5.96 g (12.14 mmol) of the hemicyanine synthesized in the previous step is placed in a 250 ml round-bottom flask together with 4.41 g (12.14 mmol) of N-(4-carboxyibutyl)-2,3,3-trimethylindoleninium-5-sulfonate sodium salt, 10.80 ml of triethylamine and 109 ml of acetic anhydride and heated at 135° C. for 2 h. The blue solution is cooled to room temperature and dropwise added to 800 ml of vigorously stirred diethyl ether. The desired product is collected on a fritted glass filter, washed with diethyl ether and dried in a desiccator under vacuum. The product is then purified by flash chromatography using a dichloromethane/methanol mixture gradient from 90/10 to 70/30. Yield is 42%. The product has absorbance maximum in ethanol at 645 nm and emission maximum at 665 nm.

Compound 4

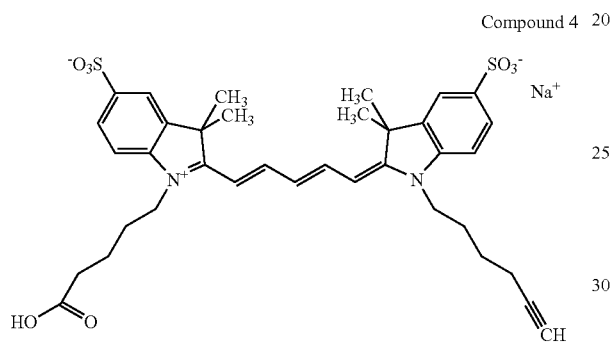

EXAMPLE 5

Synthesis of 1-(4-carboxybutyl)-1'-{6-[N,N'-difluoroboryl-1,9-dimethyl-5-(4-iodophenyl)-dipyrril]-hex-5-ynil}-3,3,3',3'-tetramethyl-5,5'-disulfonate indodicarbocyanine sodio salt (IRIS 5 alchinil-dimethylBDPY) (Compound 5)

Compound 4 and N,N'-difluoroboryl-1,9-dimethyl-5-(4-iodophenyl)-dipyrrin are reacted analogously to the procedure described in Example 2.

18.6 mg (0.044 mmol) di N,N'-difluoroboryl-1,9-dimethyl-5-(4-iodophenyl)-dipyrrin and 1.7 mg (0.0088 mmol) of CuI are placed in a vial with magnetic stirrer; 90.5 mg (0.131 mmol) of Compound 4 dissolved in the minimal quantity of dry N,N-dimethylformamide are added. Argon is refluxed for fifteen minutes. 0.012 ml (0.0088 mmol) of $N(C_2H_5)_3$ and 3.0 mg (0.0044 mmol) of $(C_6H_5)_2PdCl_2$ are added and argon is refluxed for fifteen minutes more. The reaction is conducted for eight hours under stirring at room temperature. When the time has passed, 1.7 mg (0.0088 mmol) of CuI, 0.012 mL of $N(C_2H_5)_3$ and 3.0 mg (0.0044 mmol) of $(C_6H_5)_2PdCl_2$ are added and the reaction is conducted in the same conditions 16 hours more. Purification is carried out on a MPLC column (eluents: $CH_3OH$, $H_2O$). The compound of Formula 13 is obtained.

The product appears as a blue coloured powdery solid.

EXAMPLE 6

Labelling of DNA through reaction of incorporation of 5-(cyanine IRIS 3 sulfo alkynyl)-2'-deoxycytidine triphosphate by PCR Nucleotides conjugates have been tested by PCR (Polymerase Chain Reaction) to evaluate their efficiency as substrates for the polymerase. A plasmid derived from commercial vector pBluescript II SK (Statagene), in which has been cloned a fragment of cDNA derived from human gene hGATA-3, has been used as DNA template. A fragment of the expected length of 1000 bp (base pairs) is generated using two standard T7 (forward primer) and T3 (reverse primer) oligonucleotides as primers. PCR has been conducted using several fluorescent alkynyl arm containing cyanine labelled nucleotide concentrations (from 0 to 50 μM), as summarized in the following table:

|  | Stock Conc. | Final Conc. | C+ | C− | 10 μM | 20 μM | 30 μM | 50 μM |
| --- | --- | --- | --- | --- | --- | --- | --- | --- |
| Template DNA | 1 ng/μl | 10 ng | 10 μl | — | 10 μl | 10 μl | 10 μl | 10 μl |
| 10× PCR buffer | 10× | 1× | 5 μl | 5 μl | 5 μl | 5 μl | 5 μl | 5 μl |
| $MgCl_2$ | 50 mM | 1.5 mM | 1.5 μl | 1.5 μl | 1.5 μl | 1.5 μl | 1.5 μl | 1.5 μl |
| T7 primer (Fw) | 10 μM | 0.5 μM | 2.5 μl | 2.5 μl | 2.5 μl | 2.5 μl | 2.5 μl | 2.5 μl |
| T3 primer (Rv) | 10 μM | 0.5 μM | 2.5 μl | 2.5 μl | 2.5 μl | 2.5 μl | 2.5 μl | 2.5 μl |
| d (ACT)P mix | 3.3 mM | 200 μM | 3 μl | 3 μl | 3 μl | 3 μl | 3 μl | 3 μl |
| dCTP | 0.5 mM | variable | 20 μl | 20 μl | 19 μl | 18 μl | 17 μl | 15 μl |
| 5-(cyanine IRIS 3 alkynyl)-2'-dCTP | 0.5 mM | variable | — | — | 1 μl | 2 μl | 3 μl | 5 μl |
| Taq DNA Pol | 2 U/μl | 1 U | 0.5 μl | 0.5 μl | 0.5 μl | 0.5 μl | 0.5 μl | 0.5 μl |
| $H_2O$ | — | to 5 μl | 5 μl | 15 μl | 5 μl | 5 μl | 5 μl | 5 μl |

PCR reaction has been conducted according to the following instrumental protocol, using an iCycler (Biorad) thermocycler:

STEP 1 (1 cycle)
94° C. 4 min
STEP 2 (10 cycles)
Denaturation 95° C. 1 min
"Annealing" 60° C. 1 min
After first cycle low temperature by 1.0° C. every cycle ("touch-down" method)
Extension 72° C. 1 min
STEP 3 (20 cycles)
Denaturation 95° C. 1 min
"Annealing" 50° C. 1 min
Extension 72° C. 1 min
STEP 4 (1 cycle)
4° C. infinite After PCR, ¹/₁₀ of every reaction has been tested on 0.8% agarose gel. The remaining part has been purified by means of a QIAquick PCR purification kit (Qiagen) according to the instructions supplied. The DNA has been then diluted in 120 µl of water and analyzed by means of a spectrophotometer and a fluorimeter verifying the typical absorbance and emission bands of the cyanine.

EXAMPLE 7

Conjugation of IRIS 5 alkynyl-dimethylBDPY with proteinkynase bioactive peptide The proteinkynase inhibitor bioactive peptide (available through Sigma-Aldrich) used in this example has the sequence: Thr Thr Tyr Ala Asp Phe Ile Ala Ser Gly Arg Thr Gly Arg Arg Asn Ala Ile His Asp with free terminal —NH₂ group.

29.55 mg di Compound 5 (IRIS 5 alkynyl-dimethyl-BDPY) (0.03 mmol), 12.36 mg of Dicyclohexylcarbodiimide, 6.9 mg of N-hydroxysuccinimide and 3 ml of anhydrous N,N-dimethylformamide are placed in a 50 ml single neck round-bottom flask. The reaction is conducted at 70° C. for 5 hours. When the time has passed, a solution of the bioactive peptide (133.34 mg in 2 ml of DMF) is added to the reaction mixture and reacted at room temperature overnight. The desired conjugate is obtained which is purified by medium pressure liquid chromatography (MPLC).

The invention claimed is:
1. A cyanine modified with an alkynyl-linker arm, selected from the group consisting of:

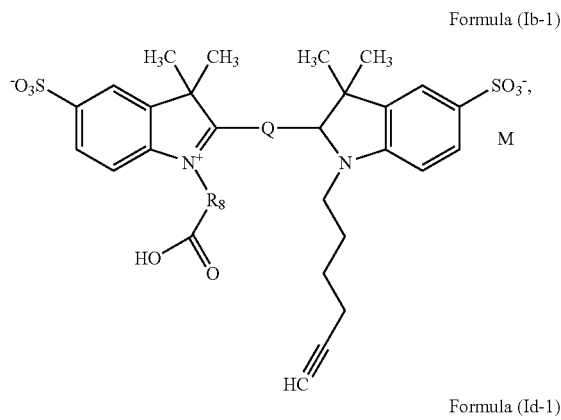

Formula (Ib-1)

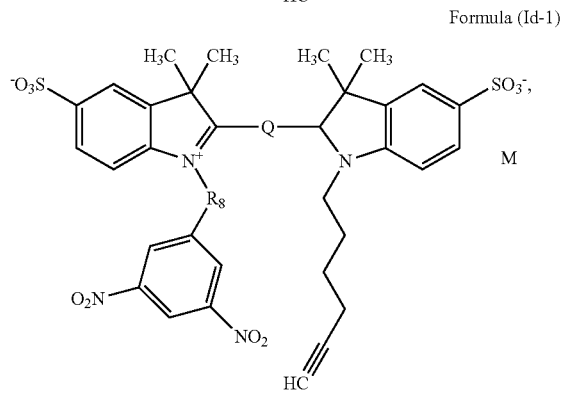

Formula (Id-1)

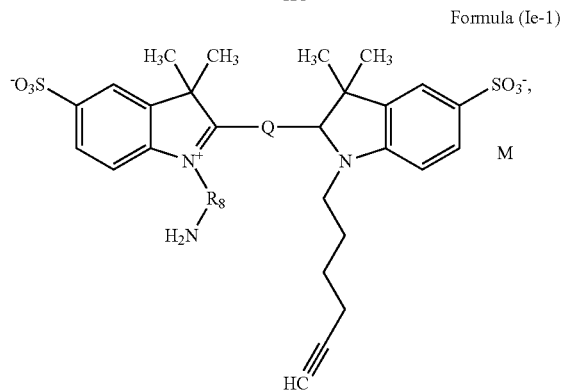

Formula (Ie-1)

SEQUENCE LISTING

<160> NUMBER OF SEQ ID NOS: 1

<210> SEQ ID NO 1
<211> LENGTH: 20
<212> TYPE: PRT
<213> ORGANISM: Homo sapiens

<400> SEQUENCE: 1

Thr Thr Tyr Ala Asp Phe Ile Ala Ser Gly Arg Thr Gly Arg Ala Asn
1               5                   10                  15

Ala Ile His Asp
            20

-continued

Formula (Im-1)

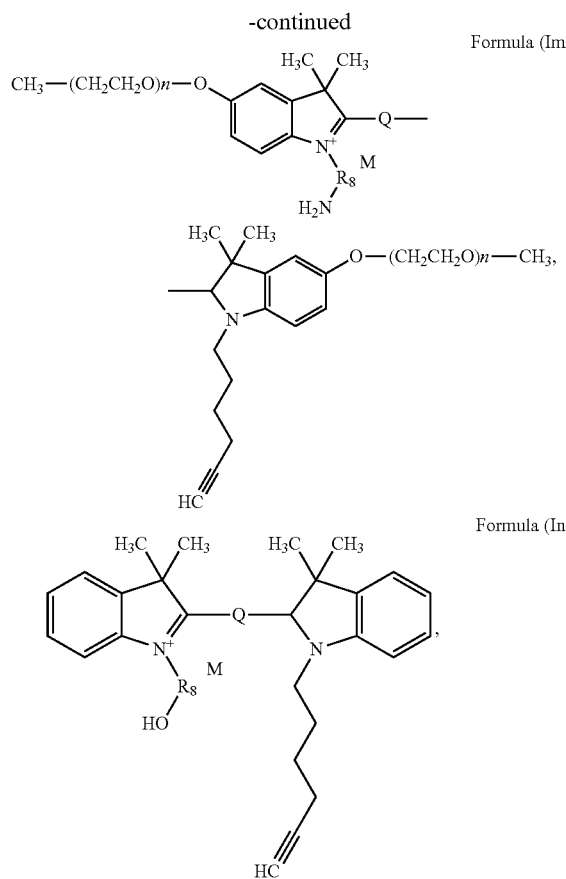

Formula (In-1)

wherein M is a counterion; $R_8$ is a linear, saturated or unsaturated alkyl chain, having from 1 to 30 carbon atoms, wherein one or more carbon atoms are each optionally substituted by a component independently selected by an oxygen or a sulfur atom, a —NH— or a —CONH— group, or a cyclic 4-, 5- or 6-membered grouping of carbon atoms, aromatic or not aromatic, wherein one or more carbon atoms are each optionally substituted by a heteroatom independently selected from oxygen, sulfur, nitrogen or selenium; Q is a polymethinic chain selected from:

wherein $R_7$ is selected from the group consisting of hydrogen, fluorine, chlorine, bromine, iodine, phenoxy, thiophenoxy, anilino, cyclohexylamino, piridine, —$R_8$—Y, —O—$R_8$—Y, —S—$R_8$—Y, —NH—$R_8$—Y, wherein Y is selected from the group consisting of carboxyl, carbonyl, amino, sulphydryl, thiocyanate, isotyocianate, isocyanate, maleimide, hydroxyl, iodoacetamido, hydrazine, aldehyde, nitrophenyl, dinitrophenyl, and trinitrophenyl, $R_8$ is as defined above, and aryl optionally substituted by one or more substituents independently selected from the group consisting of —$SO_3H$, carboxyl (—COOH), amino (—$NH_2$), carbonyl (—CHO), thiocyanate (—SCN), isothiocyanate (—CNS), epoxy and —COZ wherein Z represents a leaving group; and n is an integer between 1 and 100.

2. The cyanine according to claim 1, further comprising a second fluorescent dye, conjugated through the linker arm —$R_1$—C≡CH, wherein said second fluorescent dye is a transition metal complex with at least one heterocyclic nitrogen-containing ligand.

3. The cyanine according to claim 2, wherein said second fluorescent dye is N,N'-Difluoroboryl-1,9-dimethyl-5-(4-iodophenyl)-dipyrrin.

4. The cyanine according to claim 2, wherein said second fluorescent dye emits fluorescence at wavelengths at which the cyanine absorbs, or said fluorescent dye absorbs at wavelengths at which the cyanine emits.

* * * * *